United States Patent
Chen et al.

(10) Patent No.: US 8,697,746 B2
(45) Date of Patent: Apr. 15, 2014

(54) SOLID DISPERSION OF ALPHA-KETOAMIDE DERIVATIVES

(75) Inventors: Andrew Xian Chen, San Diego, CA (US); John Fan, San Diego, CA (US); Masazumi Yamaguchi, Kobe (JP)

(73) Assignee: Senju Pharmaceutical Co., Ltd., Osaka-shi (JP)

( * ) Notice: Subject to any disclaimer, the term of this patent is extended or adjusted under 35 U.S.C. 154(b) by 122 days.

(21) Appl. No.: 13/182,218

(22) Filed: Jul. 13, 2011

(65) Prior Publication Data

US 2012/0016020 A1  Jan. 19, 2012

Related U.S. Application Data

(60) Provisional application No. 61/364,333, filed on Jul. 14, 2010.

(51) Int. Cl.
  *A61K 31/165* (2006.01)
(52) U.S. Cl.
  USPC ............ 514/485; 424/486; 424/484; 424/488
(58) Field of Classification Search
  None
  See application file for complete search history.

(56) References Cited

U.S. PATENT DOCUMENTS

| | | | |
|---|---|---|---|
| 6,057,290 A | 5/2000 | Fukiage et al. | |
| 6,423,691 B1 | 7/2002 | Azuma et al. | |
| 7,491,705 B2 | 2/2009 | Shirasaki et al. | |
| 2002/0044967 A1 | 4/2002 | Yamashita et al. | |
| 2003/0104063 A1* | 6/2003 | Babcock et al. | 424/486 |
| 2007/0004643 A1* | 1/2007 | Shirasaki et al. | 514/19 |
| 2007/0082053 A1* | 4/2007 | Kumar | 424/486 |
| 2010/0098763 A1* | 4/2010 | Bechtold et al. | 424/486 |

FOREIGN PATENT DOCUMENTS

| | | |
|---|---|---|
| CN | 101618012 A | 1/2010 |
| JP | 2007-169226 A | 7/2007 |
| WO | 96/19239 | 6/1996 |
| WO | 99/49863 | 7/1999 |
| WO | 99/44624 | 9/1999 |
| WO | 03/000294 A1 | 1/2003 |
| WO | 2005/056519 A1 | 6/2005 |
| WO | 2012008159 | 1/2012 |

OTHER PUBLICATIONS

ISR, Written Opinion, Publication and Documents cited in ISR of corresponding PCT application No. PCT/JP2011/004021, (Oct. 2011).

Wang, KKW and PW Yuen, Calpain inhibition: an overview of its therapeutic potential, Trends in Pharmacological Sciences, 1994, vol. 15, p. 412.

Ansari Muhammad Tayyab et al., "Physicochemical Characterization of Artemether Solid Dispersions with Hydrophilic Carriers by Freeze Dried and Melt Methods", Archives of Pharmacal Research (Seoul), vol. 33, No. 6, Jun. 2010, pp. 901-910.

(Continued)

*Primary Examiner* — Brandon Fetterolf
*Assistant Examiner* — Theodore R West
(74) *Attorney, Agent, or Firm* — Hogan Lovells US LLP (57) ABSTRACT

A solid dispersion comprising ((1S)-1-((((1S)-1-benzyl-2,3-dioxo-3-(cyclopropylamino)propyl)amino)carbonyl)-3-methylbutyl)carbamic acid 5-methoxy-3-oxapentyl ester made amorphous in the presence of a water-soluble cellulosic polymer has improved storage stability. The solid dispersion also has improved solubility for an improved bioavailability.

12 Claims, 4 Drawing Sheets

(56) References Cited

OTHER PUBLICATIONS

Koumura A et al., "A Novel Calpain Inhibitor, ((1S)-1-((((1S)-1-benzyl-3-cyclopropylamino 2, 3-di-oxopropyl)amino) carbonyl)-3-methylbutyl)c arbamic acid 5-methoxy-3-oxapentyl ester, protects neuronal cells from cerebral ischemia-induced damage in mice", Neuroscience, New York, NY, US, vol. 157, No. 2, Nov. 19, 2008, pp. 309-318.

* cited by examiner

SOLID DISPERSION OF ALPHA-KETOAMIDE DERIVATIVES

This is a Non-Provisional application, which claims priority to U.S. Provisional Application 61/364,333, filed on Jul. 14, 2010, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a solid dispersion of ((1S)-1-((((1S)-1-benzyl-2,3-dioxo-3-(cyclopropylamino)propyl) amino)carbonyl)-3-methylbutyl)carbamic acid 5-methoxy-3-oxapentyl ester having an improved solubility and dissolution.

BACKGROUND ART

α-ketoamide derivatives, such as ((1s)-1-((((1s)-1-benzyl-2,3-dioxo-3-(cyclopropylamino)propyl)amino)carbonyl)-3-methylbutyl)carbamic acid 5-methoxy-3-oxapentyl ester, are useful as calpain inhibitors (see Patent Literature 1). It has been revealed that a calpain inhibitor is involved in various diseases, such as cerebral apoplexy, subarachnoid hemorrhage, Alzheimer's disease, ischemic disease, muscular dystrophy, cataract, platelet aggregation disorder, arthritis, and the like (see Non-Patent Literature 1). In particular, usability of calpain inhibitors as ophthalmic agents for various eye diseases has been disclosed (see Patent Literatures 2 and 3). On the other hand, in order to orally administer a drug having low solubility and low absorption, making the drug into such a form as to improve its solubility is required for maximum exertion of the pharmacological effect thereof. Means of improving the solubility and absorption of a drug by making the drug amorphous with the use of polymers or the like are known (see Patent Literatures 4 to 7).

CITATION LIST

[Patent Literature 1] WO 2005/56519 (U.S. Pat. No. 7,491,705)
[Patent Literature 2] WO 99/44624 (U.S. Pat. No. 6,423,691)
[Patent Literature 3] U.S. Pat. No. 6,057,290
[Patent Literature 4] WO 99/049863 (US20020044967)
[Patent documents 5] JP 2007-169226 A
[Patent Literature 6] WO 2003/000294 (US2003104063)
[Patent Literature 7] WO 96/019239 (AU4314196)
[Non Patent Literature 1] Trends in Pharmacological Sciences, 1994, vol. 15, p. 412

SUMMARY OF INVENTION

Technical Problem ((1S)-1-((((1S)-1-benzyl-2,3-dioxo-3-(cyclopropylamino) propyl)amino)carbonyl)-3-methylbutyl)carbamic acid 5-methoxy-3-oxapentyl ester is a compound having a calpain inhibitory activity, which is well absorbed orally and exhibits an adequately sustained blood level. An object of the present invention is to provide a solid dispersion of ((1S)-1-((((1S)-1-benzyl-2,3-dioxo-3-(cyclopropylamino)propyl) amino)carbonyl)-3-methylbutyl)carbamic acid 5-methoxy-3-oxapentyl ester having an improved solubility for a further improved absorption of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester.

Solution to Problem

The present inventors have conducted various investigations in order to achieve the above object, and found that a solid dispersion of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester having an improved solubility in solvent, such as water, can be provided by making amorphous ((1S)-1-((((1S)-1-benzyl-2,3-dioxo-3-(cyclopropylamino)propyl) amino)carbonyl)-3-methylbutyl)carbamic acid 5-methoxy-3-oxapentyl ester in the presence of a water-soluble cellulosic polymer. The inventors also found that, surprisingly, dissolving a ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance and a water-soluble cellulosic polymer in a solvent, such as water/t-butyl alcohol, followed by lyophilization makes the amorphous ((1S)-1-((((1S)-1-benzyl-2,3-dioxo-3-(cyclopropylamino)propyl)amino) carbonyl)-3-methylbutyl)carbamic acid 5-methoxy-3-oxapentyl ester to give a stable solid dispersion of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester having an improved solubility in an industrially advantageous manner. The present inventors have wholeheartedly continued investigations and finally completed the present invention.

Namely, the present invention relates to:

[1] a solid dispersion comprising ((1S)-1-((((1S)-1-benzyl-2,3-dioxo-3-(cyclopropylamino)propyl)amino)carbonyl)-3-methylbutyl)carbamic acid 5-methoxy-3-oxapentyl ester made amorphous in the presence of a water-soluble cellulosic polymer;

[2] the solid dispersion according to the above [1], wherein the water-soluble cellulosic polymer is at least one kind selected from hydroxypropyl methylcellulose, hydroxypropyl cellulose, and hydroxyethyl cellulose;

[3] the solid dispersion according to the above [1], wherein the water-soluble cellulosic polymer is hydroxypropyl methylcellulose;

[4] the solid dispersion of the above [1], wherein the concentration of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester relative to the solid dispersion is within the range of 40 to 60% by mass;

[5] a solid composition comprising the solid dispersion of the above [1], further comprising an excipient selected from the group comprising a bulking agent, a binder, a disintegrant, a lubricant, a glidant and solubilizing agent;

[6] a method for improving the solubility of ((1S)-1-((((1S)-1-benzyl-2,3-dioxo-3-(cyclopropylamino)propyl) amino) carbonyl)-3-methylbutyl)carbamic acid 5-methoxy-3-oxapentyl ester by making the amorphous ((1S)-1-((((1S)-1-benzyl-2,3-dioxo-3-(cyclopropylamino)propyl)amino) carbonyl)-3-methylbutyl) carbamic acid 5-methoxy-3-oxapentyl ester in the presence of a water-soluble cellulosic polymer; and

[7] a method for producing a solid dispersion comprising ((1S)-1-((((1S)-1-benzyl-2,3-dioxo-3-(cyclopropylamino) propyl) amino)carbonyl)-3-methylbutyl)carbamic acid 5-methoxy-3-oxapentyl ester in the presence of a water-soluble cellulosic polymer, the method comprising the steps of:

(1) dissolving ((1S)-1-((((1S)-1-benzyl-2,3-dioxo-3-(cyclopropylamino)propyl)amino)carbonyl)-3-methylbutyl)carbamic acid 5-methoxy-3-oxapentyl ester in a solvent, (2) dissolving a water-soluble cellulosic polymer in the solution obtained in (1), and (3) lyophilizing the solution obtained in (2).

ADVANTAGEOUS EFFECTS OF INVENTION

According to the present invention, a solid dispersion of ((1S)-1-((((1S)-1-benzyl-2,3-dioxo-3-(cyclopropylamino) propyl) amino)carbonyl)-3-methylbutyl)carbamic acid 5-methoxy-3-oxapentyl ester having storage stability and an improved solubility for a further improved oral absorption can be prepared. In more detail, according to the present invention, a solid dispersion of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester having an improved solubility can be manufactured in an industrially advantageous manner by making amorphous ((1S)-1-((((1S)-1-benzyl-2,3-dioxo-3-(cyclopropylamino)propyl)amino) carbonyl)-3-methylbutyl)carbamic acid 5-methoxy-3-oxapentyl ester in the presence of a water-soluble cellulosic polymer, such as hydroxypropyl methylcellulose, hydroxypropyl cellulose, and hydroxyethyl cellulose.

DESCRIPTION OF EMBODIMENTS

The present invention provides a solid dispersion comprising amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester made in the presence of a water-soluble cellulosic polymer.

((1S)-1-((((1S)-1-benzyl-2,3-dioxo-3-(cyclopropylamino)propyl)amino)carbonyl)-3-methylbutyl)carbamic acid 5-methoxy-3-oxapentyl ester used for the present invention is a known crystalline compound, manufactured according to a known method, for example, as in WO 2005/056519. In the present invention, a crystalline ((1S)-1-((((1S)-1-benzyl-2,3-dioxo-3-(cyclopropylamino)propyl)amino)carbonyl)-3-methylbutyl)carbamic acid 5-methoxy-3-oxapentyl ester manufactured as mentioned above is termed a ((1S)-1-((((1S)-1-benzyl-2,3-dioxo-3-(cyclopropylamino)propyl) amino)carbonyl)-3-methylbutyl)carbamic acid 5-methoxy-3-oxapentyl ester drug substance.

The water-soluble cellulosic polymer compound used for the present invention is not particularly limited and any kind can be used unless it is against the spirit of the present invention, and preferably at least one kind selected from the group consisting of hydroxyethyl cellulose, hydroxypropyl methylcellulose (HPMC), hydroxypropyl cellulose, carboxymethyl cellulose, methyl cellulose, and the salts thereof. More preferably, the compound is hydroxypropyl methylcellulose, for example, HPMC2906 or 2910.

In the case where hydroxypropyl methylcellulose is selected, the viscosity of a 2% aqueous solution thereof is usually 2 to 100000 mPa·s, and preferably 4 to 10000 mPa·s.

The blending ratio of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and a water-soluble cellulosic polymer is usually about 20:80 to about 80:20 (mass ratio), and preferably about 40:60 to about 60:40 (mass ratio). The compound used in the present invention is characterized by being made amorphous in the presence of a water-soluble cellulosic polymer.

The present invention provides a solid dispersion comprising amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester made in the presence of a water-soluble cellulosic polymer. The solid dispersion of the present invention means a composition wherein a solid ((1S)-1-((((1S)-1-benzyl-2,3-dioxo-3-(cyclopropylamino)propyl)amino)carbonyl)-3-methylbutyl) carbamic acid 5-methoxy-3-oxapentyl ester is dispersed in a solid water-soluble cellulosic polymer. The ((1S)-1-((((1S)-1-benzyl-2,3-dioxo-3-(cyclopropylamino)propyl)amino) carbonyl)-3-methylbutyl) carbamic acid 5-methoxy-3-oxapentyl ester is most preferably molecularly dispersed, preferably completely made amorphous form, or at least partially made amorphous form.

In the present invention, the solid composition may comprise, in addition to the above-described solid dispersion, a bulking agent, a binder, a disintegrant, a lubricant, a glidant, a solubilizing agent, or a combination thereof.

Examples of the bulking agent include starch, crystalline cellulose, and lactose; examples of the binder include polyvinyl pyrrolidone; examples of the disintegrant include croscarmellose sodium; examples of the lubricant include magnesium stearate; examples of the glidant include talc, and fine silicon dioxide; and examples of the solubilizing agent include polyethylene glycol, polyvinyl pyrrolidone, and lecithin.

The optimum amount of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester added to 1 unit of the solid composition is usually 1 to 1000 mg, and preferably 100 to 600 mg. Here, 1 unit means 1 tablet, 1 packet of granules, or 1 capsule.

The content of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester in the solid composition is preferably about 20 to 80% by mass, and more preferably about 40 to 60% by mass.

The solid composition comprising a solid dispersion of amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester made in the presence of water-soluble cellulosic polymer may be formed into granules or tablets according to a known method. Alternatively, the solid composition may be encapsulated in capsules (for example, size 000) for administration, or may be mixed with an aqueous medium and used as a liquid preparation, such as an ophthalmic solution and an injectable solution.

The present invention further provides a method for improving the solubility of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester by making the amorphous ((1S)-1-((((1S)-1-benzyl-2,3-dioxo-3-(cyclopropylamino)propyl)amino)carbonyl)-3-methylbutyl) carbamic acid 5-methoxy-3-oxapentyl ester in the presence of a water-soluble cellulosic polymer.

The solubility of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester in a solvent, such as water, and the bioavailability thereof can be improved by making the amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester in the presence of a water-soluble cellulosic polymer and using it in the form of a solid dispersion comprising the amorphous compound.

The solid dispersion may be in the form of a solid composition comprising a bulking agent, a binder, a disintegrant, a lubricant, a glidant, or a solubilizing agent. In the present invention, improving solubility means making ((1S)-1-((((1S)-1-benzyl-2,3-dioxo-3-(cyclopropylamino)propyl)amino)carbonyl)-3-methylbutyl)carbamic acid 5-methoxy-3-oxapentyl ester into a form with a solubility higher than that of crystalline ((1S)-1-((((1S)-1-benzyl-2,3-dioxo-3-(cyclopropylamino)propyl)amino) carbonyl)-3-methylbutyl)carbamic acid 5-methoxy-3-oxapentyl ester. As for the degree of improvement in solubility, the solubility of the improved ((1S)-1-((((1S)-1-benzyl-2,3-dioxo-3-(cyclopropylamino)propyl)amino)carbonyl)-3-methylbutyl)carbamic acid 5-methoxy-3-oxapentyl ester is preferably increased by 1.5-fold or more, and more preferably by 2-fold or more as compared with that of a crystalline ((1S)-1-((((1S)-1-benzyl-2,3-dioxo-3-(cyclopropylamino)propyl)amino)carbonyl)-3-methylbutyl)carbamic acid 5-methoxy-3-oxapentyl ester, at least at a point of time within 60 minutes from the start of dissolution test.

The water-soluble cellulosic polymer compound used for the present invention is not particularly limited and any kind can be used unless it is against the spirit of the present invention, but the above-mentioned compounds are preferable.

The present invention further provides a method for producing a solid dispersion of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester comprising a water-soluble cellulosic polymer.

The solid dispersion of the present invention may be prepared by any method as long as the dispersion is a composition comprising amorphous ((1S)-1-((((1S)-1-benzyl-2,3-dioxo-3-(cyclopropylamino)propyl)amino)carbonyl)-3-methylbutyl) carbamic acid 5-methoxy-3-oxapentyl ester made in the presence of a water-soluble cellulosic polymer. By dissolving a ((1S)-1-((((1S)-1-benzyl-2,3-dioxo-3-(cyclopropylamino)propyl)amino) carbonyl)-3-methylbutyl) carbamic acid 5-methoxy-3-oxapentyl ester drug substance, which is usually crystalline, and a water-soluble cellulosic polymer in a solvent capable of making both compounds dissolve thereinto to prepare a solution of ((1S)-1-((((1S)-1-benzyl-2,3-dioxo-3-(cyclopropylamino)propyl)amino) carbonyl)-3-methylbutyl)carbamic acid 5-methoxy-3-oxapentyl ester and subsequently removing the solvent by a known method, such as lyophilization, reduced-pressure evaporation, or spray drying, an amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester can be obtained as a solid dispersion. The solvent may be any kind as long as it is capable of making ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and a water-soluble cellulosic polymer dissolve thereinto, but preferably a polar solvent, such as, an alcohol, water, tetrahydrofuran, and preferably a mixture of an alcohol and water. The alcohol is preferably t-butyl alcohol in particular. The blending ratio of the alcohol and water is about 90:10 to about 10:90 (volume ratio), preferably about 90:10 to about 60:40 (volume ratio), and more preferably about 90:10 to about 80:20 (volume ratio).

For solvent removal, lyophilization, reduced-pressure evaporation with the use of an evaporator, or spray drying may be performed by a known method.

In the case where a bulking agent, a binder, a disintegrant, a lubricant, a glidant, or a solubilizing agent is added to the above-mentioned solid dispersion to form a solid composition, these additive ingredients may be mixed into the solid dispersion, or added with ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and a water-soluble cellulosic polymer to the above-mentioned solution.

((1S)-1-((((1S)-1-benzyl-2,3-dioxo-3-(cyclopropylamino) propyl)amino)carbonyl)-3-methylbutyl)carbamic acid 5-methoxy-3-oxapentyl ester contained in the solid composition of the present invention is useful for diseases, such as ischemic disease, immunopathy, multiple sclerosis, Alzheimer disease, osteoporosis, disease by brain tissue hindrance, cataract, glaucoma, retina disease, chorioretinal disease, complicating disease of the posterior-segment-of-eyeball by photocoagulation, and disease accompanied by vascularization. The dosage amount of ((1S)-1-((((1S)-1-benzyl-2,3-dioxo-3-(cyclopropylamino) propyl)amino)carbonyl)-3-methylbutyl)carbamic acid 5-methoxy-3-oxapentyl ester can be determined by a doctor considering disease name, disease condition, age, etc.

As used herein, % expresses % by mass unless otherwise stated.

EXAMPLES

Test Example 1

In order to improve the solubility of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester, a solid dispersion was prepared by making an amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester in the presence of dispersant of a water-soluble polymer etc. The influence of making ((1S)-1-((((1S)-1-benzyl-2,3-dioxo-3-(cyclopropylamino) propyl)amino)carbonyl)-3-methylbutyl)carbamic acid 5-methoxy-3-oxapentyl ester a solid dispersion on the solubility thereof was investigated using, as an index, the amount of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester dissolved in a certain amount of water.

Operation Procedure

Preparation of Samples

Formulations 2 to 6 were prepared as follows: In a mixed solution of 85 mL of t-butyl alcohol (Sigma-Aldrich) and 15 mL of water, 2.3 g of a ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance was dissolved. To this mixture, 2.3 g of one kind of the additives shown in Table 1 (water-soluble polymer etc.) was added. The obtained solution of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester was lyophilized through freezing at −30° C. and removal of solvent by reduced pressure (20 mmHg or lower) with the use of a lyophilizer (Virtis Advantage lyophilizer) to give a solid dispersion. In the case of Formulation 1, without addition of any additive, 2.3 g of the ((1S)-1-((((1S)-1-benzyl-2,3-dioxo-3-(cyclopropylamino)propyl) amino)carbonyl)-3-methylbutyl)carbamic acid 5-methoxy-3-oxapentyl ester drug substance was lyophilized.

The ((1S)-1-((((1S)-1-benzyl-2,3-dioxo-3-(cyclopropylamino) propyl)amino)carbonyl)-3-methylbutyl)carbamic acid 5-methoxy-3-oxapentyl ester drug substance used here was synthesized from phenylalanine, diethylene glycol monomethyl ether (DGME), and leucine as starting materials in accordance with the production method described in WO 2005/056519.

Method for Measuring Dissolved Amount of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester Each of the above-prepared Formulation 1 and the solid dispersions of Formulations 2 to 6 was separately dispersed in water. Sampling from each solution was performed at 15, 30, and 60 minutes after dispersion, and the concentration of ((1S)-1-((((1S)-1-benzyl- 2,3-dioxo-3-(cyclopropylamino) propyl)amino) carbonyl)-3-methylbutyl)carbamic acid 5-methoxy-3-oxapentyl ester was measured according to the procedure shown below.

Procedure of Measuring Dissolved Amount of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester To 5 mg of each of the above-prepared Formulation 1 and the solid dispersions of Formulations 2 to 6, 1 mL of water was added and the mixture was shaken with a shaker (Labindustries Inc., Labquake Shaker L1237). Shaking was stopped when the predetermined sampling time elapsed, and centrifugation at 13000 rpm was immediately performed at 25° C. for 5 minutes with a centrifugal separator (Kendro Lab Products, Sorvall Biofuge Fresco) to give a supernatant. A sample solution was prepared by mixing 0.5 mL of methanol to 0.5 mL of the supernatant and then measured for concentration of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester by HPLC (Shimadzu, 10A-VP system).
HPLC conditions:
Detector: ultraviolet absorptiometer (detection wavelength: 252 nm)
Column: YMC-Pack ODS-A (inside diameter: 4.6 mm, length: 250 mm, particle diameter: 5 μm, YMC)
Column temperature: constant temperature at around 40° C.
Mobile phase: methanol/water/acetic acid (60:40:5)
Flow rate: 1.0 mL/min (retention time of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester: about 10 to 14 min)

TABLE 1

| | Formulation Example | | | | | |
|---|---|---|---|---|---|---|
| | 1 | 2 | 3 | 4 | 5 | 6 |
| ((1S)-1-((((1S)-1-benzyl-2,3-dioxo-3-(cyclopropylamino)propyl)amino)carbonyl)-3-methylbutyl)carbamic acid 5-methoxy-3-oxapentyl ester | 100% | 50% | 50% | 50% | 50% | 50% |
| Hydroxypropyl methylcellulose 2910 (The Dow Chemical Company, Methocel E5LV*) | | 50% | | | | |
| Polyethylene glycol (PEG8000, Dow Chemical Company, Carbowax 8000 NF, FCC) | | | 50% | | | |
| Lactose (Foremost, FastFlo) | | | | 50% | | |
| Polyvinyl pyrrolidone (BASF, Kollidon 12PF) | | | | | 50% | |
| Lecithin (PHOSPHOLIPID, Phospholipon 90H) | | | | | | 50% |
| Total | 100% | 100% | 100% | 100% | 100% | 100% |

*The viscosity of the 2% solution was 4 to 6 mPa · s.

Powder X-Ray Diffraction

Powder X-ray diffraction (Spectris, X'Pert PRO MPD) was performed for the ((1S)-1-((((1S)-1-benzyl-2,3-dioxo-3-(cyclopropylamino)propyl)amino)carbonyl)-3-methylbutyl) carbamic acid 5-methoxy-3-oxapentyl ester drug substance and Formulations 2 to 6 to confirm whether the ((1S)-1-((((1S)-1-benzyl-2,3-dioxo-3-(cyclopropylamino)propyl) amino)carbonyl)-3-methylbutyl) carbamic acid 5-methoxy-3-oxapentyl ester was made amorphous form. In the case where diffraction peaks specific to the raw crystalline ((1S)-

1-((((1S)-1-benzyl-2,3-dioxo-3-(cyclopropylamino)propyl)amino)carbonyl)-3-methylbutyl)carbamic acid 5-methoxy-3-oxapentyl ester (2θ: 7.6, 10.6, 13.8, 15.0, 17.2, 17.6, 19.3, 21.3, 22.9, 23.7, and 24.6) were broaden or weakened, the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester was judged to be made amorphous form. The measurement conditions were as follows.

Powder X-ray diffraction measurement conditions:

Target: copper

X-ray tube current: 40 mA

X-ray tube voltage: 45 kV

Scan range: 2θ=4.0 to 45°

Step: 2θ=0.01671°

Average time/step: 10.160 s

Fixed divergence slit: ½°

Results

Figure 1:
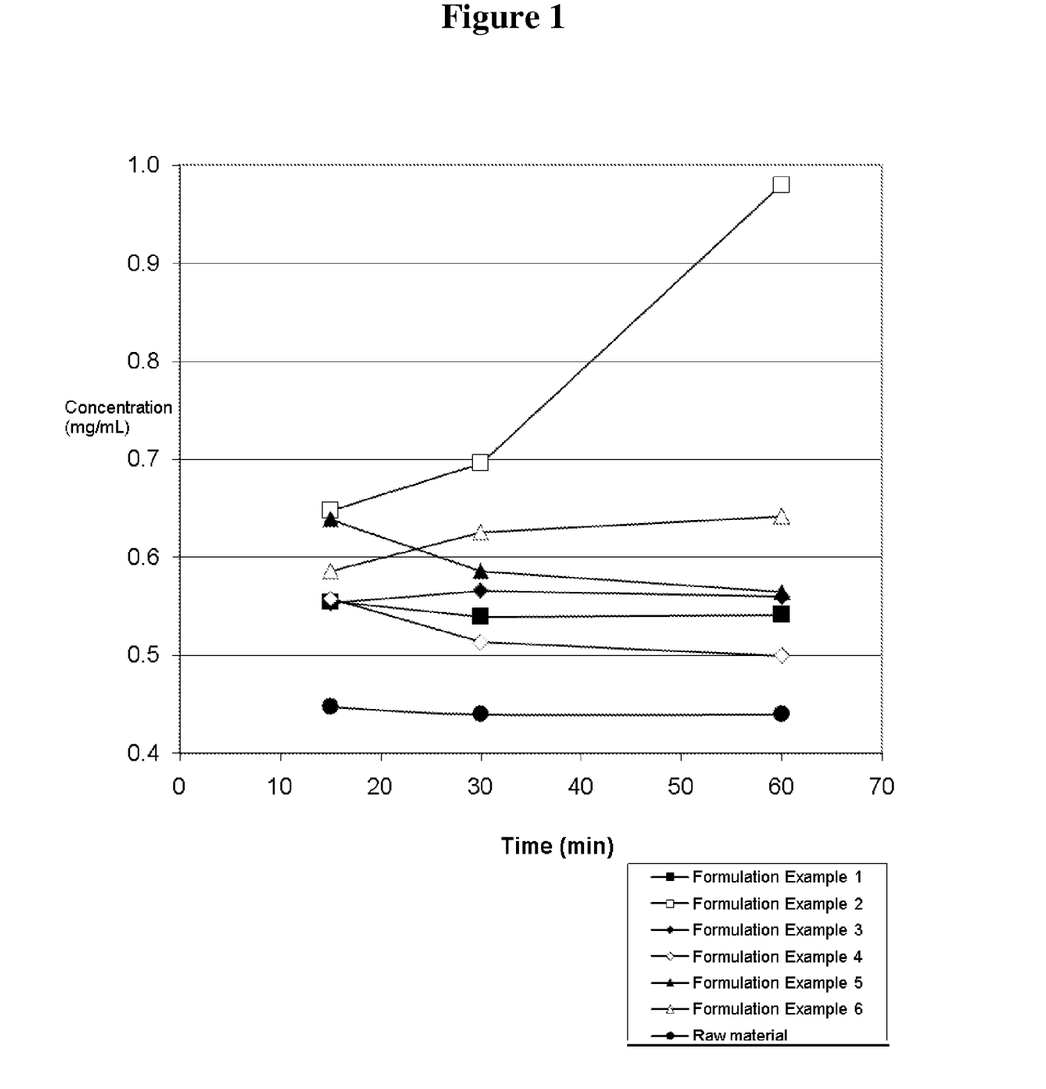
FIG. 1 is a graph showing the relationship between the elapsed time and the dissolved amounts of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester of Formulation Examples 1 to 6 in Test Example 1.

From the results of powder X-ray diffraction, it was confirmed that the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance was crystalline. It was also confirmed that ((1S)-1-((((1S)-1-benzyl-2,3-dioxo-3-(cyclopropylamino)propyl)amino)carbonyl)-3-methylbutyl)carbamic acid 5-methoxy-3-oxapentyl ester was made amorphous form in the presence of a dispersant, such as hydroxypropyl methylcellulose, polyethylene glycol, lactose, polyvinyl pyrrolidone and Lecithin. The results of the dissolved amount measurement are shown in FIG. 1.

Whereas the dissolved amount of the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance in water was 0.45 mg/mL, ((1S)-1-((((1S)-1-benzyl-2,3-dioxo-3-(cyclopropylamino)propyl)amino)carbonyl)-3-methylbutyl) carbamic acid 5-methoxy-3-oxapentyl ester made amorphous form in the presence of the above-mentioned dispersant had an increased solubility of 0.5 to 1.0 mg. Inter alia, Formulation Example 2, which was a solid dispersion prepared by blending equal amounts of the ((1S)-1-((((1S)-1-benzyl-2,3-dioxo-3-(cyclopropylamino) propyl)amino)carbonyl)-3-methylbutyl)carbamic acid 5-methoxy-3-oxapentyl ester drug substance and hydroxypropyl methylcellulose, showed a solubility increased by about 2-fold as compared with that of the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance.

It was confirmed that ((1S)-1-((((1S)-1-benzyl-2,3-dioxo-3-(cyclopropylamino)propyl)amino)carbonyl)-3-methylbutyl)carbamic acid 5-methoxy-3-oxapentyl ester made amorphous form in the presence of each dispersant had an improved solubility as compared to ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance. In particular, it was found that the solid dispersion comprising ((1S)-1-((((1S)-1-benzyl-2,3-dioxo-3-(cyclopropylamino)propyl)amino) carbonyl)-3-methylbutyl) carbamic acid 5-methoxy-3-oxapentyl ester made amorphous in the presence of hydroxypropyl methylcellulose had an extremely improved solubility.

Test Example 2

Solid dispersions having different blending ratios of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and hydroxypropyl methylcellulose were prepared. The influence of different blending ratios of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and hydroxypropyl methylcellulose on the solubility of ((1S)-1-((((1S)-1-benzyl-2,3-dioxo-3-(cyclopropylamino)propyl)amino) carbonyl)-3-methylbutyl)carbamic acid 5-methoxy-3-oxapentyl ester was evaluated using, as an index, the amount of ((1S)-1-((((1S)-1-benzyl-2,3-dioxo-3-(cyclopropylamino)propyl)amino) carbonyl)-3-methylbutyl)carbamic acid 5-methoxy-3-oxapentyl ester dissolved in a certain amount of water.

Operation Procedure

Preparation of Samples

In a mixed solution of 123 mL of t-butyl alcohol (TBA) and 17 mL of water, 3.2 g of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance was dissolved. To the mixture, 3.2 g (Formulation Example 7), 4.8 g (Formulation Example 8), or 2.1 g (Formulation Example 9) of hydroxypropyl methylcellulose shown in Table 2 was added. The obtained ((1S)-1-((((1S)-1-benzyl-2,3-dioxo-3-(cyclopropylamino) propyl)amino)carbonyl)-3-methylbutyl)carbamic acid 5-methoxy-3-oxapentyl ester solution was lyophilized. The lyophilization was performed through freezing of the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester solution at −30° C. and removal of solvent by distillation under reduced pressure (20 mmHg or lower) (for 10 hours at 0 degree C. and 20 to 30 hours at 25 degree C.) with the use of a lyophilizer (Virtis Advantage lyophilizer).

The ((1S)-1-((((1S)-1-benzyl-2,3-dioxo-3-(cyclopropylamino) propyl)amino)carbonyl)-3-methylbutyl)carbamic acid 5-methoxy-3-oxapentyl ester drug substance used was prepared by the same production method as shown in Test Example 1.

TABLE 2

| | Formulation Example | | |
|---|---|---|---|
| | 7 | 8 | 9 |
| ((1S)-1-((((1S)-1-benzyl-2,3-dioxo-3-(cyclopropylamino)propyl)amino)carbonyl)-3-methylbutyl)carbamic acid 5-methoxy-3-oxapentyl ester | 50% | 40% | 60% |
| Hydroxypropyl methylcellulose 2910 (The Dow Chemical Company, Methocel E5LV*) | 50% | 60% | 40% |
| Total | 100% | 100% | 100% |

*The viscosity of the 2% solution was 4 to 6 mPa · s.

Method for Measuring Dissolved Amount of ((1S)-1-((((1S)-1-benzyl-2,3-dioxo-3-(cyclopropylamino) propyl)amino)carbonyl)-3-methylbutyl)carbamic acid 5-methoxy-3-oxapentyl ester Each of the solid dispersion of the above-prepared Formulations 7 to 9 was separately dispersed in water. A sample was taken from each solution at 30, 60, and 120 minutes after dispersion and measured for the concentration of ((1S)-1-((((1S)-1-benzyl-2,3-dioxo-3-(cyclopropylamino)propyl) amino) carbonyl)-3-methylbutyl)carbamic acid 5-methoxy-3-oxapentyl ester by the same method as in Test Example 1.

Results

Figure 2:
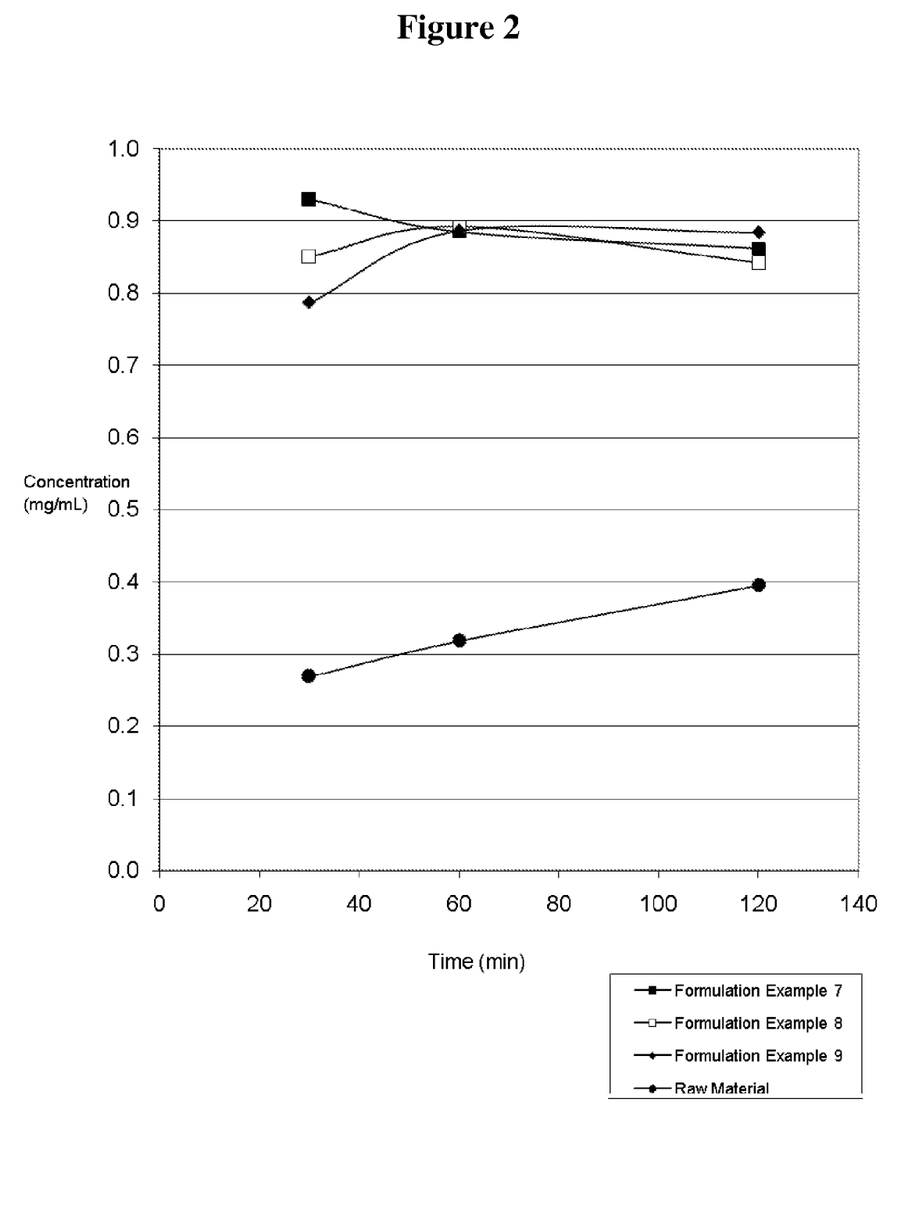
FIG. 2 is a graph showing the relationship between the elapsed time and the dissolved amounts of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester of Formulation Examples 7 to 9 in Test Example 2.

The results are shown in FIG. 2. It was shown that when the blending ratio of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester and hydroxypropyl methylcellulose was within the range of 40:60 to 60:40 (mass ratio), the obtained solid dispersion had an improved solubility as compared with the ((1S)-1-((((1S)-1-benzyl-2, 3-dioxo-3-(cyclopropylamino)propyl)amino)carbonyl)-3-methylbutyl)carbamic acid 5-methoxy-3-oxapentyl ester drug substance.

Test Example 3

In order to evaluate the influence of compression on the dissolution property of a solid composition comprising the solid dispersion of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester made amorphous in the presence of hydroxypropyl methylcellulose, the dissolved amount from a compressed and an uncompressed one of the solid composition into water was measured. The dissolution rate was calculated from the dissolved amount.

Operation Procedure

Preparation of Samples

To a mixed solution of 85 mL of t-butyl alcohol and 15 mL of water (volume ratio 85:15), 6.7 g (Formulation Examples 10) or 6.7 g (Formulation Examples 11) of the water-soluble polymer shown in Table 3 was added and dissolved thereinto with high speed stirring. To this, 10 g of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester drug substance was added and dissolved by heating to 60° C. The lyophilization was performed through freezing of the solution at −30° C. and removal of solvent by sublimation under reduced pressure (20 mmHg or lower) with the use of a lyophilizer (Virtis Advantage lyophilizer). The obtained dry composition was pulverized with a tabletop blender (Cuisinart, Grind Central model DCG12BC) and sifted through a 25-mesh sieve. The obtained solid compositions were each divided into 2, composition to be compressed (C) and composition not to be compressed (NC), and then each put into capsules (CapsulGel, gelatin, size 000), which were used as solid compositions. The compressed formulation was prepared by light manual compression with a stainless-steel tamper.

The ((1S)-1-((((1S)-1-benzyl-2,3-dioxo-3-(cyclopropylamino) propyl)amino)carbonyl)-3-methylbutyl)carbamic acid 5-methoxy-3-oxapentyl ester drug substance used was prepared by the same production method as shown in Test Example 1.

TABLE 3

| | Formulation Example 10 | | | Formulation Example 11 | | |
|---|---|---|---|---|---|---|
| | % | mg/unit | mg/g | % | mg/unit | mg/g |
| ((1S)-1-((((1S)-1-benzyl-2,3-dioxo-3-(cyclopropylamino)propyl)amino)carbonyl)-3-methylbutyl)carbamic acid 5-methoxy-3-oxapentyl ester | 50.25% | 250 | 503 | 40.9% | 250 | 409 |
| Hydroxypropyl methylcellulose 2910 (The Dow Chemical Company, Methocel E5LV*) | 33.45% | 166.5 | 335 | 27.3% | 166.9 | 273 |
| Starch (Colorcon, STARCH 1500) | 10.25% | 50 | 103 | 20.6% | 125.9 | 206 |
| Fine silicon dioxide (Cabot Corporation, Cab-O-Sil, M-5P) | 0.73% | 3.5 | 7.3 | 1.0% | 6.1 | 10 |
| Croscarmellose sodium (FMC Biopolymer, Ac-Di-Sol) | 5.32% | 25 | 53 | 10.2% | 62.3 | 102 |
| Total | 100% | 495 | 1000 | 100% | 611.2 | 1000 |

*The viscosity of the 2% solution was 4 to 6 mPa · s.

Method for Measuring Eluted Amount of ((1S)-1-((((1S)-1-benzyl-2,3-dioxo-3-(cyclopropylamino) propyl)amino)carbonyl)-3-methylbutyl)carbamic acid 5-methoxy-3-oxapentyl ester The uncompressed solid composition and the compressed solid composition were separately put into capsules, and according to the USP dissolution test Apparatus 2 (the paddle method), using water as the test solution, the dissolution of ((1S)-1-((((1S)-1-benzyl-2,3-dioxo-3-(cyclopropylamino) propyl)amino)carbonyl)-3-methylbutyl)carbamic acid 5-methoxy-3-oxapentyl ester from 1 capsule into water was tested. That is, while the test solution was kept at 37° C. and the paddle was rotated at 100 rpm, the test solution was sampled at 20, 40, and 60 minutes from the start of the test, and the concentration of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester was measured by HPLC on the conditions described in Test Example 1. Since the amounts of the solid composition in a capsule and the test solution used in the test differed, the following formula was used to calculate dissolution rate, which means the dissolved amount per unit weight of the composition.

Dissolution rate (%)=(drug concentration×volume of test solution)/(mass of drug in 1 capsule)

Results

Figure 3:
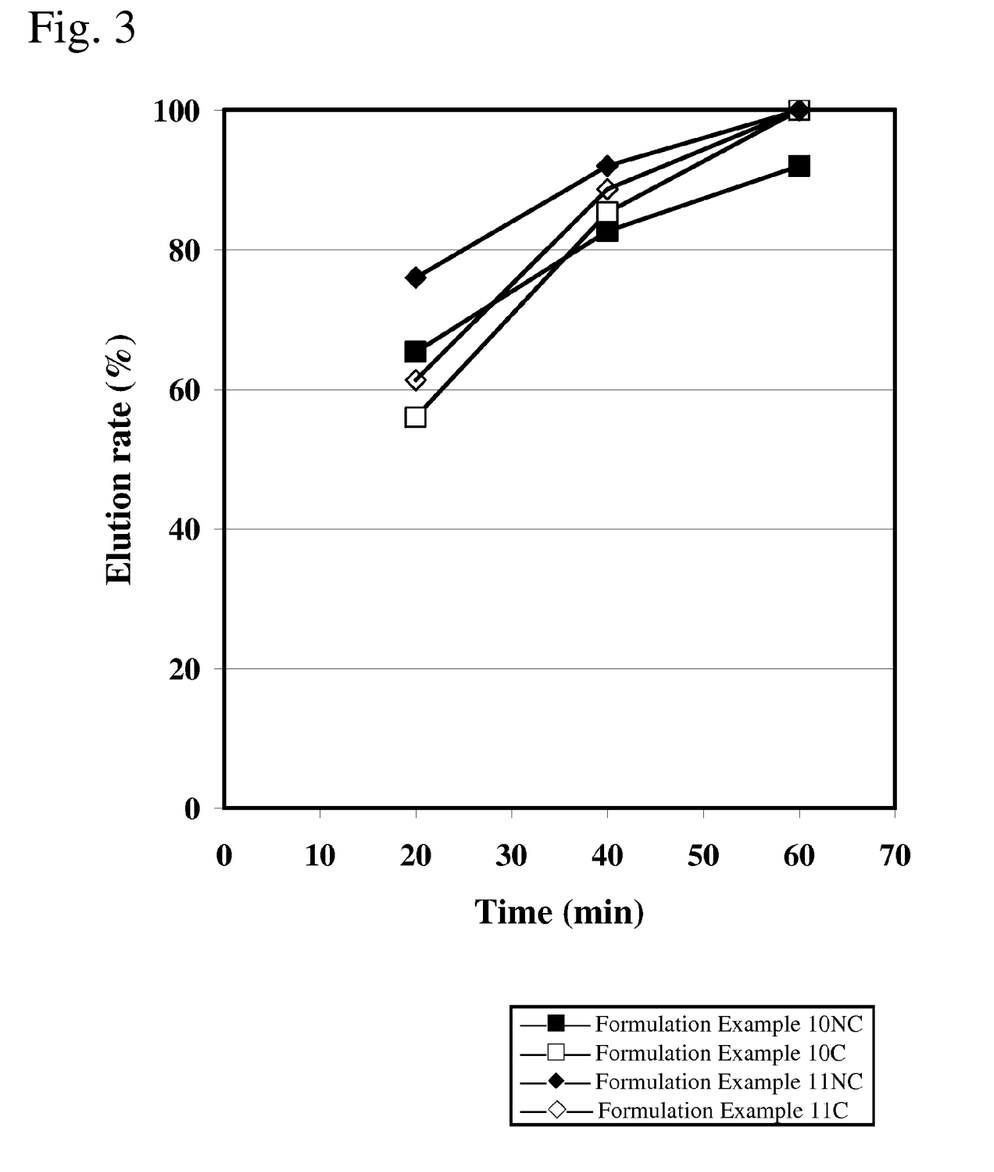
FIG. 3 is a graph showing the relationship between the elapsed time and the dissolution rate of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester of Formulation Examples 10 and 11 in Test Example 3.

The results are shown in FIG. 3. The compressed Formulation Example 10C and Formulation Example 11C were compared with the uncompressed Formulation Example 10NC and Formulation Example 11NC. The results showed no significant difference in the dissolution rates, that is, the dissolution rates of the solid compositions containing solid dispersions of ((1S)-1-((((1S)-1-benzyl-2,3-dioxo-3-(cyclopropylamino)propyl) amino)carbonyl)-3-methylbutyl)carbamic acid 5-methoxy-3-oxapentyl ester into water were not affected by compression.

Test Example 4

Hydroxypropyl methylcellulose, hydroxypropyl cellulose, and hydroxyethyl cellulose was used to prepare a solid dispersion of ((1S)-1-((((1S)-1-benzyl-2,3-dioxo-3-(cyclopropylamino)propyl) amino)carbonyl)-3-methylbutyl)carbamic acid 5-methoxy-3-oxapentyl ester in the presence of one of these water-soluble cellulosic polymers. The solubility of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester in the solid dispersion was evaluated using, as an index, the amount of ((1S)-1-((((1S)-1-benzyl-2,3-dioxo-3-(cyclopropylamino)propyl) amino)carbonyl)-3-methylbutyl)carbamic acid 5-methoxy-3-oxapentyl ester dissolvable in a certain amount of water.

Operation Procedure

Preparation of Samples

To prepare Formulation Example 1, 10 g of ((1S)-1-((((1S)-1-benzyl-2,3-dioxo-3-(cyclopropylamino)propyl) amino)carbonyl)-3-methylbutyl)carbamic acid 5-methoxy-3-oxapentyl ester drug substance was added to a mixed solution of 85 mL of t-butyl alcohol and 15 mL of water (volume ratio 85:15) and dissolved by heating to 60° C. To prepare Formulation examples 2, 12, and 13, 10 g of each water-soluble cellulosic polymer shown in Table 4 was separately added to a mixed solution of 85 mL of t-butyl alcohol and 15 mL of water (volume ratio 85:15) and dissolved with high speed stirring. To this mixture, 10 g of ((1S)-1-((((1S)-1-benzyl-2,3-dioxo-3-(cyclopropylamino)propyl)amino) carbonyl)-3-methylbutyl)carbamic acid 5-methoxy-3-oxapentyl ester drug substance was added and dissolved by heating to 60° C. The solutions of Formulation Examples 1, 2, 12, and 13 were lyophilized through freezing at −30° C. and removal of solvent by sublimation under reduced pressure (20 mmHg or lower) for 48 hours at room temperature) with the use of a lyophilizer (YAMATO SCIENTIFIC, DW-185II C, PHIL, and DP32) to give solid dispersions.

The ((1S)-1-((((1S)-1-benzyl-2,3-dioxo-3-(cyclopropylamino) propyl)amino)carbonyl)-3-methylbutyl)carbamic acid 5-methoxy-3-oxapentyl ester drug substance used was prepared by the same production method as shown in Test Example 1.

TABLE 4

| | Formulation Example | | | |
|---|---|---|---|---|
| | 1 | 2 | 12 | 13 |
| ((1S)-1-((((1S)-1-benzyl-2,3-dioxo-3-(cyclopropylamino)propyl)amino)carbonyl)-3-methylbutyl)carbamic acid 5-methoxy-3-oxapentyl ester | 100% | 50% | 50% | 50% |
| Hydroxypropyl methylcellulose 2910 (Shin-Etsu Chemical, TC-5S) | | 50% | | |
| Hydroxypropyl cellulose (Wako Pure Chemical Industries, 1st grade) | | | 50% | |
| Hydroxyethyl cellulose (Wako Pure Chemical Industries, 1st grade) | | | | 50% |
| Total | 100% | 100% | 100% | 100% |

Method for Measuring Dissolved Amount of ((1S)-1-((((1S)-1-benzyl-2,3-dioxo-3-(cyclopropylamino) propyl)amino)carbonyl)-3-methylbutyl)carbamic acid 5-methoxy-3-oxapentyl ester Each of the above-prepared Formulation 1 and the solid dispersions of Formulations 2, 12, and 13 was separately dispersed in water. A sample was taken from each solution at 15, 30, and 60 minutes after dispersion and measured for the concentration of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester according to the procedure shown below.

Operation for Measuring Dissolved Amount of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester To 5 mg of each of the above-prepared Formulation 1 and the solid dispersions of Formulations 2, 12, and 13, 1 mL of water was added and the mixture was shaken with a shaker (AS ONE, MW-1). Shaking was stopped when the predetermined sampling time elapsed, and centrifugation at 12000 rpm was immediately performed for 5 minutes with a centrifugal separator (TOMY, MCX-150) to give a supernatant. A sample solution was prepared by adding 0.5 mL of methanol to 0.5 mL of the supernatant and then measured by HPLC (Shimadzu, 10A-VP system). The measurement conditions of HPLC were the same as in Test Example 1.

Powder X-Ray Diffraction

Powder X-ray diffraction (Spectris, X'Pert PRO MPD) was performed for the ((1S)-1-((((1S)-1-benzyl-2,3-dioxo-3-(cyclopropylamino)propyl)amino)carbonyl)-3-methylbutyl) carbamic acid 5-methoxy-3-oxapentyl ester drug substance and the above-prepared Formulations 1, 2, 12, and 13 by the same method as in Test Example 1 to confirm whether the ((1S)-1-((((1S)-1-benzyl-2,3-dioxo-3-(cyclopropylamino) propyl)amino)carbonyl)-3-methylbutyl)carbamic acid 5-methoxy-3-oxapentyl ester was made amorphous. Whether the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester was made amorphous or not was judged based on the criteria shown in Test Example 1.

Results

Figure 4:
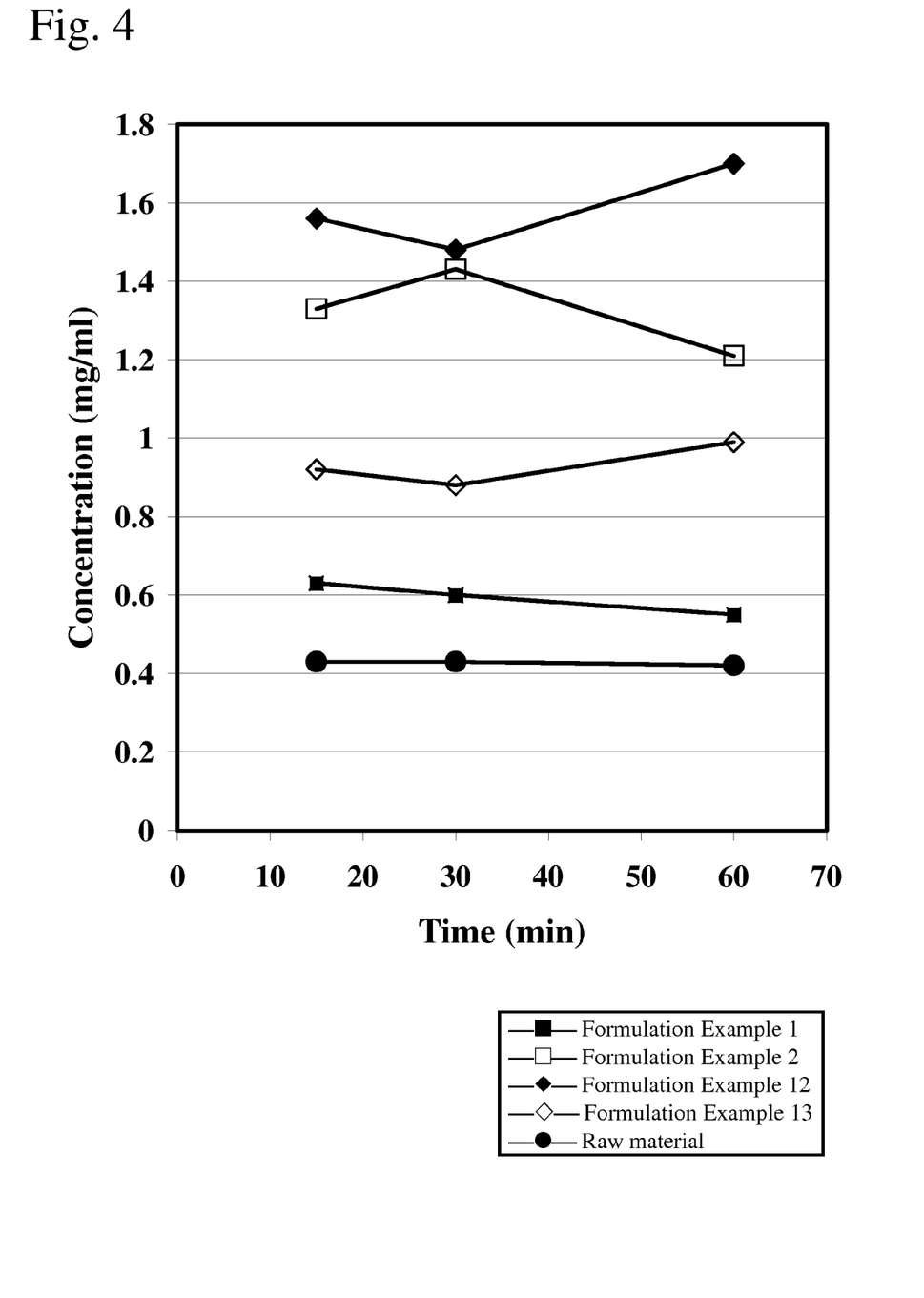
FIG. 4 is a graph showing the relationship between the elapsed time and the dissolved amounts of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester of Formulation Examples 1, 2, 12, and 13 in Test Example 4.

The results of X-ray diffraction confirmed that Formulations 1, 2, 12, and 13 were made amorphous. The results of the dissolved amount measurement are shown in FIG. 4. The Formulations 2, 12, and 13 to which hydroxypropyl methylcellulose, hydroxypropylcellulose, and hydroxyethyl cellulose were added, respectively, showed dissolved amounts of ((1S)-1-((((1S)-1-benzyl-2,3-dioxo-3-(cyclopropylamino)propyl) amino)carbonyl)-3-methylbutyl)carbamic acid 5-methoxy-3-oxapentyl ester increased by about 2- to 3-fold as compared with that of the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance. It was confirmed that the solubility of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester in water was improved by making the amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester in the presence of these water-soluble cellulosic polymers and using it in the form of a solid dispersion comprising the amorphous form. Meanwhile, Formulation Example 1, to which no water-soluble cellulosic polymer was added, showed no significant increase in solubility although ((1S)-1-((((1S)-1-benzyl-2,3-dioxo-3-(cyclopropylamino) propyl)amino)carbonyl)-3-methylbutyl) carbamic acid 5-methoxy-3-oxapentyl ester therein was made amorphous.

Preparation Example

Preparation of Samples

In a mixed solution of 85 mL of t-butyl alcohol and 15 mL of water, the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester drug substance in 10 times the unit amount shown in Table 5 was dissolved. To this mixture, the ingredients shown in Table 4 in 10 times the unit amount were added to give a solution of ((1S)-1-((((1S)-1-benzyl-2,3-dioxo-3-(cyclopropylamino)propyl)amino)carbonyl)-3-methylbutyl) carbamic acid 5-methoxy-3-oxapentyl ester. The solution was lyophilized through freezing at −30° C. and removal of solvent by sublimation under reduced pressure (20 mmHg or lower) to give a solid composition. As for Formulation Example 3, before the step of lyophilization, part of the solution was separated and subjected to spray drying to give a solid composition.

TABLE 5

Formulation Examples 1 to 6 (mg/unit)

| Ingredient | Preparation Example | | | | | |
|---|---|---|---|---|---|---|
| | 1 | 2 | 3 | 4 | 5 | 6 |
| ((1S)-1-((((1S)-1-benzyl-2,3-dioxo-3-(cyclopropylamino)propyl)amino)carbonyl)-3-methylbutyl)carbamic acid 5-methoxy-3-oxapentylester | 250 | 250 | 370 | 306 | 282.6 | 250 |
| Hydroxypropyl methylcellulose 2910 (viscosity: 4 mPa · s) | 167 | | | | | |
| Hydroxypropyl methylcellulose 2910 (viscosity: 10000 mPa · s) | | | | | 188.4 | |
| Hydroxypropyl methylcellulose 2906 | | 166.9 | | | | |
| Methyl cellulose | | | 62.5 | | | |
| Hydroxyethyl cellulose | | | | 204 | | |
| Carboxymethylcellulose sodium | | | | | | 167 |
| Starch | | 125.9 | 25 | 42 | | |
| Fine silicon dioxide | 10 | 6.1 | 7.5 | 12 | 11.4 | 10 |
| Croscarmellose sodium | 40 | 62.3 | 25 | 30 | 55.8 | 40 |
| Mannitol | 30 | | | | | 30 |
| Magnesium stearate | 5 | | 10 | 6 | 3 | 5 |
| Total | 502 | 611.2 | 500 | 600 | 600 | 502 |

The invention claimed is:

1. A solid dispersion comprising ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and a water-soluble cellulosic polymer, wherein the water-soluble cellulosic polymer is at least one kind selected from hydroxypropyl methylcellulose and hydroxypropyl cellulose.

2. The solid dispersion according to claim 1, wherein the water-soluble cellulosic polymer is hydroxypropyl methylcellulose.

3. The solid dispersion of claim 1, wherein the concentration of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester relative to the solid dispersion is within the range of 40 to 60% by mass.

4. A solid composition comprising the solid dispersion of claim 1, further comprising an excipient selected from the group comprising a bulking agent, a binder, a disintegrant, a lubricant, a glidant and solubilizing agent.

5. A method for producing a solid dispersion comprising ((1S)-1-((((1S)-1-benzyl-2,3-dioxo-3-(cyclopropylamino)propyl)amino)carbonyl)-3-methylbutyl)carbamic acid 5-methoxy-3-oxapentyl ester in the presence of a water-soluble cellulosic polymer, the method comprising the steps of:
    (1) dissolving ((1S)-1-((((1S)-1-benzyl-2,3-dioxo-3-(cyclopropylamino)propyl)amino)carbonyl)-3-methylbutyl)carbamic acid 5-methoxy-3-oxapentyl ester in a solvent,
    (2) dissolving a water-soluble cellulosic polymer in the solution obtained in (1), wherein the water-soluble cellulosic polymer is at least one kind selected from hydroxypropyl methylcellulose and hydroxypropyl cellulose, and
    (3) lyophilizing the solution obtained in (2).

6. A method for improving the solubility of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester comprising the steps of:
    1) dissolving ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and a water-soluble cellulosic polymer in a solvent, wherein the water-soluble cellulosic polymer is at least one polymer selected from the group consisting of hydroxypropyl methylcellulose and hydroxypropyl cellulose, and 2) removing the solvent to obtain amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester.

7. The method according to claim 6, wherein the solvent is capable of dissolving both the ((1S)-1-((((1S)-1-benzyl-2,3-dioxo-3-(cyclopropylamino)propyl)amino)carbonyl)-3-methylbutyl)carbamic acid 5-methoxy-3-oxapentyl ester and the water-soluble cellulosic polymer.

8. The method according to claim 6, wherein the water-soluble cellulosic polymer is hydroxypropyl methylcellulose.

9. The method according to claim 6, wherein the amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester is in a solid dispersion and the amorphous ((1S)-1-((((1S)-1-benzyl-2,3-dioxo-3-(cyclopropylamino)propyl)amino)carbonyl)-3-methylbutyl)carbamic acid 5-methoxy-3-oxapentyl ester is in a concentration of the solid dispersion within the range of 40 to 60% by mass.

10. The method according to claim 7, wherein the solvent is a mixture of an alcohol and water.

11. The method according to claim 10, wherein the alcohol is t-butyl alcohol.

12. The method according to claim 6, wherein the solvent is removed by lyophilization.

* * * * *